(12) United States Patent
Lee et al.

(10) Patent No.: US 9,220,793 B2
(45) Date of Patent: Dec. 29, 2015

(54) METHODS FOR IN VIVO IDENTIFICATION OF CANCER INITIATING CELLS BY MULTIMODALITY REPORTER GENE IMAGING

(75) Inventors: Yi-Jang Lee, Taipei (TW); Shiau-Yi Wang, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 117 days.

(21) Appl. No.: 13/525,016

(22) Filed: Jun. 15, 2012

(65) Prior Publication Data

US 2013/0336880 A1 Dec. 19, 2013

(51) Int. Cl.
*C12Q 1/68* (2006.01)
*A61K 49/00* (2006.01)
*A61K 51/00* (2006.01)
*A61K 51/04* (2006.01)

(52) U.S. Cl.
CPC ............ *A61K 49/00* (2013.01); *A61K 49/0008* (2013.01); *A61K 51/00* (2013.01); *A61K 51/0491* (2013.01)

(58) Field of Classification Search
None
See application file for complete search history.

(56) References Cited

PUBLICATIONS

Kettlun et al (The American Society of Gene & Cell Therapy: vol. 19 No. 9 pp. 1636-1644, Sep. 2011, published online Jul. 5, 2011).*
Bonizzoni et al (Insect Molecular Biology 2007 vol. 16, No. 5, pp. 645-650).*
Kai Tao et al., Imagable 4T1 model for the study of late stage breast cancer, BMC Cancer, Aug. 9, 2008, pp. 1-19.
Ilaria Chiodi, et al., Drug Treatment of Cancer Cell Lines: A Way to Select for Cancer Stem Cells?, Cancers, Mar. 4, 2011, pp. 1111-1128, vol. 3, ISSN. 2072-6694.
Erina Vlashi et al., In Vivo Imaging, Tracking, and Targeting of Cancer Stem Cells, Articles/JNCI, Mar. 4, 2009, pp. 350-359, vol. 101, Issue 5.
Lori S. Hart et al., Invincible, but Not Invisible: Imaging Approaches Toward In Vivo Detection of Cancer Stem Cells, Journal of Clinical Oncology, Jun. 10, 2088, pp. 2901-2910, vol. 26, No. 17, American Society of Clinical Oncology, Jun. 10, 2008.
Pritha Ray, Multimodality molecular imaging of disease progression in living subjects, J.Biosci, Aug. 2011, pp. 499-504, vol. 36, No. 3, Indian Accademy of Sciences.
Moritz F. Kircher et al., Nonivasive cell-tracking methods, Reviews, Nov. 2011, pp. 677-688, vol. 8.
Kate W. R. Broadley et al., Side Population is Not Necessary or Sufficient for a Cancer Stem Cell Phenotype in Glioblastoma Multiforme, Stem Cells, Jan. 14, 2011, pp. 452-461, vol. 29.
Shiau-Yi, et al., Use of PiggyBac Transposon for the Multimodality Molecular Imaging on Murine Breast Cancer Model and Identify the Population of Cancer Stem Cells, Department of Biomedical Imaging and Radiological Sciences, National Yang-Ming University, Taipei, Taiwan, Jun. 17, 2011, one page.

* cited by examiner

*Primary Examiner* — Catherine S Hibbert
(74) *Attorney, Agent, or Firm* — Muncy, Geissler, Olds & Lowe, P.C.

(57) ABSTRACT

The present invention relates to a method for detecting cancer initiating cells in living animal body by multimodality reporter gene imaging. In the method of this invention, cells escaping from cell loss during tumor enlargement are identified as cancer initiating cells.

9 Claims, 10 Drawing Sheets
(7 of 10 Drawing Sheet(s) Filed in Color)

SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: mRFP forward primer

<400> SEQUENCE: 1
ccatgggctg ggaggcctcc                                                    20

<210> SEQ ID NO 2
<211> LENGTH: 22
<212> TYPE: DNA
<213> ORGANISM: Artificial
<220> FEATURE:
<223> OTHER INFORMATION: mRFP reverse primer

<400> SEQUENCE: 2
ttaaccctag aaagatagtc tg                                                 22

<210> SEQ ID NO 3
<211> LENGTH: 18
<212> TYPE: DNA
<213> ORGANISM: Artificial
<220> FEATURE:
<223> OTHER INFORMATION: Oct4 forward primer

<400> SEQUENCE: 3
accgagtgag aggcaacc                                                      18

<210> SEQ ID NO 4
<211> LENGTH: 20
<212> TYPE: DNA
<213> ORGANISM: Artificial
<220> FEATURE:
<223> OTHER INFORMATION: Oct4 reverse primer

<400> SEQUENCE: 4
tgagaaagga gacccagcag                                                    20

<210> SEQ ID NO 5
<211> LENGTH: 21
<212> TYPE: DNA
<213> ORGANISM: Artificial
<220> FEATURE:
<223> OTHER INFORMATION: Sox2 forward primer

<400> SEQUENCE: 5
cgagtggaaa cttttgtcgg a                                                  21

<210> SEQ ID NO 6
<211> LENGTH: 15
<212> TYPE: DNA
<213> ORGANISM: Artificial
<220> FEATURE:
<223> OTHER INFORMATION: Sox2 reverse primer

<400> SEQUENCE: 6
tgtgcagcgt cgcag                                                         15

<210> SEQ ID NO 7
<211> LENGTH: 22
<212> TYPE: DNA
<213> ORGANISM: Artificial

```
<220> FEATURE:
<223> OTHER INFORMATION: Human/mouse beta actin forward primer

<400> SEQUENCE: 7
ggaaatcgtg cgtgacatta ag                                          22

<210> SEQ ID NO 8
<211> LENGTH: 20
<212> TYPE: DNA
<213> ORGANISM: Artificial
<220> FEATURE:
<223> OTHER INFORMATION: Human/mouse beta actin reverse primer

<400> SEQUENCE: 8
ggccatctct tgctcgaagt                                             20
```

METHODS FOR IN VIVO IDENTIFICATION OF CANCER INITIATING CELLS BY MULTIMODALITY REPORTER GENE IMAGING

FIELD OF THE INVENTION

The present invention relates to a method for in vivo identification of cancer initiating cells by imaging-based technology. In particular, this invention related to the use of multimodality reporter gene imaging for in vivo tracking living cells that escape cell loss during tumor progression and are identified as cancer initiating cells, or cells containing the characteristics of cancer initiating cells.

BACKGROUND OF THE INVENTION

Tumor growth is dependent on a kinetic model that is based on the progression of cell proliferation and cell loss. The parameters for cell proliferation during tumor progression include the cell cycle time (Tc), growth fraction (GF), and potential tumor doubling time (Tpot). In contrast, the cell-loss factor is determined by Tpot and the actual time for doubling of the tumor volume (Td) (Steel G G., 1967, *Eur J Cancer* 3(4):381-387). The causes of cell loss include malnutrition and lack of oxygen caused by rapid proliferation, necrosis and apoptosis, immunological attack, escape from the primary site, and exfoliation (Cooper E H, et al., 1975, *Advances in cancer research* 21:59-120). These conditions can be regarded as stresses for cells residing in a rapidly growing tumor. Whether cells escaping from these stresses inherit or obtain resistance abilities is unknown.

The tracking and characterization of live cells in a tumor are important for cancer treatment. Reporter gene imaging is an indirect approach to labeling cells for imaging-based in vivo tracking and targeting by different modalities (Serganova I, et al., 2008, *Handb Exp Pharmacol* (185 Pt 2): 167-223). This method is especially important for tracking cell viability in vivo because gene transcription and translation occur only in live cells (Acton P D, Zhou R., 2005, *J Nucl Med Mol Imaging* 49(4): 349-360). In addition, the transmission of genes to progeny is in principle not diminished or diluted if the reporter genes can replicate within the genomes of host cells (Kircher M F, et al., 2011, *Nat Rev Clin Oncol* 8(11): 677-688). Firefly luciferase and fluorescent proteins are canonical reporter genes used for bioluminescent imaging and optical imaging, respectively. For radionuclide-based reporter gene imaging, herpes simplex virus type 1-thymidine kinase (HSV1-tk) is commonly used because it can uptake a broad range of radiolabeled nucleoside analogues for imaging the target cells in vivo (Diehn M, Clarke M F, 2006, *J Natl Cancer Inst* 98(24):1755-1757). Expression of the HSV1-tk reporter gene can be used for live cell tracking by positron emission tomography (PET) or single photon emission computed tomography (SPECT), depending on the types of radionuclide-labeled substrates. Multimodality reporter gene imaging using co-expressed luciferase/fluorescent proteins and HSV1-tk has been reported to be a powerful tool for basic biological and preclinical research (Love Z, Wang F, Dennis J, et al., 2007, *J Nucl Med* 48(12):2011-2020; Ray P., 2011, *Curr Pharm Biotechnol* 12(4):539-546). In addition, PET and SPECT can be merged with computed tomography (CT) to obtain functional/anatomic imaging with high sensitivity and spatial resolution.

Cancer stem cells (CSCs, or cancer initiating cells) belong to the hierarchy model that a subset of rare cell population inherits stem cell-like characteristics, including self-renewal and generation of non-tumorigenic progeny (Reya T, et al., 2001, *Nature* 414(6859):105-111). This theory has intrigued many researchers in recent years because CSCs are resistant to chemo-radiotherapy and are likely to be the cause of tumor recurrence and metastasis (Zhang M, Rosen J M. 2006, *Curr Opin Genet Dev* 16(1):60-64). However, the identification of CSCs in vivo remains a challenge because of the lack of suitable markers for this purpose. If CSCs naturally resist environmental stresses, it would be speculated that this population may also escape from cell loss during tumor progression. More evidence is required to support this hypothesis.

SUMMARY OF THE INVENTION

This invention is based on the surprisingly discovery that the remnant live cells in late-stage tumors exhibit the characteristics of cancer initiating cell. These findings may provide estimations for the tendency of advanced tumors to disseminate to distant organs and exhibit chemo- and radio-resistance.

In one aspect, the present invention features a method for in vivo identification of cancer initiating cells, which comprises tracking living cells that escape cell loss during tumor progression and identified as cancer initiating cells by imaging-based technology. The method of the invention comprises the steps of: providing a multimodality reporter gene imaging system for co-expressing multiple reporter genes; integration of the multiple reporter genes into chromosomal DNA of target cancer cells; and tracking the tumor progression and location of living target cancer cells that escape cell loss during tumor progression by multimodality reporter gene imaging.

In one embodiment of the invention, the multimodality reporter gene imaging comprises fluorescence and radionuclide-based imaging. In certain embodiments of the invention, the reporter gene may be a fluorescence protein gene, a luciferase gene, or a non-substrate specific thymidine kinase gene.

In one embodiment of the invention, a non-viral piggyBac transposition system is exploited to establish stable cell lines expressing herpes simplex virus type 1-thymidine kinase (HSV1-tk) and monomeric red fluorescence protein (mRFP) reporter genes for radionuclide-based imaging and optical imaging, respectively. Unlike conventional stable transfection methods, selection with drugs (such as puromycin) is not required to obtain stable clones. This approach is important because it greatly avoids drug-induced clonal variation and mutation.

In another aspect, this invention features a diagnostic method for tumor resistance to a cancer therapy, comprising the integration of multiple reporter genes into chromosomal DNA of target cancer cells; and tracking remnant live cells in the tumor mass during the cancer therapy by multimodality reporter gene imaging.

Other features or advantages of the present invention will be apparent from the following drawings and detailed description of several embodiments, and also from the appending claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 (A) Tracking of mRFP expression in sorted 4T1-PB-2R/PBase cells in a time-course manner. 4T1-PB-2R cells were used as a control; the mRFP signal in these cells disappeared after 7 days of culture. FIG. 2 (B) Western blot analysis for HSV1-tk expression in sorted 4T1-PB-2R/PBase cells cultured for 60 days compared to 4T1-PB-2R cells and parental cells. FIG. 2 (C) Cell uptake assay to detect HSV1-tk activity in cells treated with $^3$H-FIAU. The data represent the means of three independent experiments ±S.D. *: $p<0.05$. FIG. 2 (D) ATT assay for detecting viability of cells exposed to different concentrations of GCV. Each datum represents the means of five independent experiments ±S.D. *: $p<0.05$. FIG. 2 (E) Genomic PCR for amplifying the mRFP DNA sequence from cellular chromosomes. P.C., a positive control by amplifying the mRFP gene from the PB-2R-puro plasmid. FIG. 2 (F) FISH for visualizing the integration of the mRFP reporter gene in the chromosomes of 4T1-PB-2R/PBase cells.

FIG. 3 (A) The growth rates of tumors formed by 4T1-PB-2R/PBase cells and 4T1-PB-2R cells were measured and compared using calipers (N=6). FIG. 3 (B) Upper panel: the IVIS50 system for imaging the level of the mRFP signal in tumors one day and seven days after initial seeding. The ROIs are indicated by yellow circles. Lower panel: quantification of the imaging results revealed a correlation between the number of initial cells seeded and the intensity of the fluorescent signals in the formed tumors. FIG. 3 (C) Comparison of mRFP and HSV1-tk expression in tumor sections from two cell types.

FIG. 4 (A) Optical imaging of mRFP expression from 1 to 21 days after 4T1-PB-2R/PBase cells and 4T1-PB-2R cells were s.c. injected into BALB/c mice. FIG. 4 (B) Quantification of photon signal determined by ROIs of optical imaging. Each data point represents a mean of three independent values ±S.D. *: $p<0.05$ compared between tumors formed by two stable cell lines with or without reporter gene expression (N=3). FIG. 4 (C) MicroSPECT/CT imaging of HSV1-tk expression in live cells in formed tumors between week 1 and week 4. FIG. 4 (D) 3-D imaging reconstruction for live cells expressing HSV1-tk based on microSPECT/CT data. FIG. 4 (E) MicroPET/CT imaging showed $^{18}$F-FDG uptake in tumors with or without HSV1-tk expression. FIG. 4 (F) Frozen sections were stained with H&E to distinguish the live tissues (left panel) and necrotic region (right panel) in the primary tumor.

FIG. 5 (A) Comparison of sphere formation in 4T1 parental cells and ex vivo isolated remnant live cells (day 2 and day 4 after addition of conditional medium). FIG. 5 (B) Quantification of mammospheres. The sphere numbers were obtained from four random fields examined under the microscope.

FIG. 6 (C) Luciferase reporter gene assay for investigating the Oct4 transcriptional activity in parental cells and isolated remnant live cells. The data represent the means of four independent experiments ±S.D. *: $p<0.05$. FIG. 6 (D) Western blot analysis to compare the expression of Oct4, Sox2, and CD133 proteins between each cell line.

DETAILED DESCRIPTION OF THE INVENTION

In the present invention, multimodality reporter gene imaging is provided to track live cells during tumor progression. The remnant live cells in late-stage tumors are identified to exhibit CSCs-like characteristics.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Example 1

Construction of PiggyBac Transduced Multiple Imaging Animal Model

Plasmids and Stable Transfection

Figure 1:
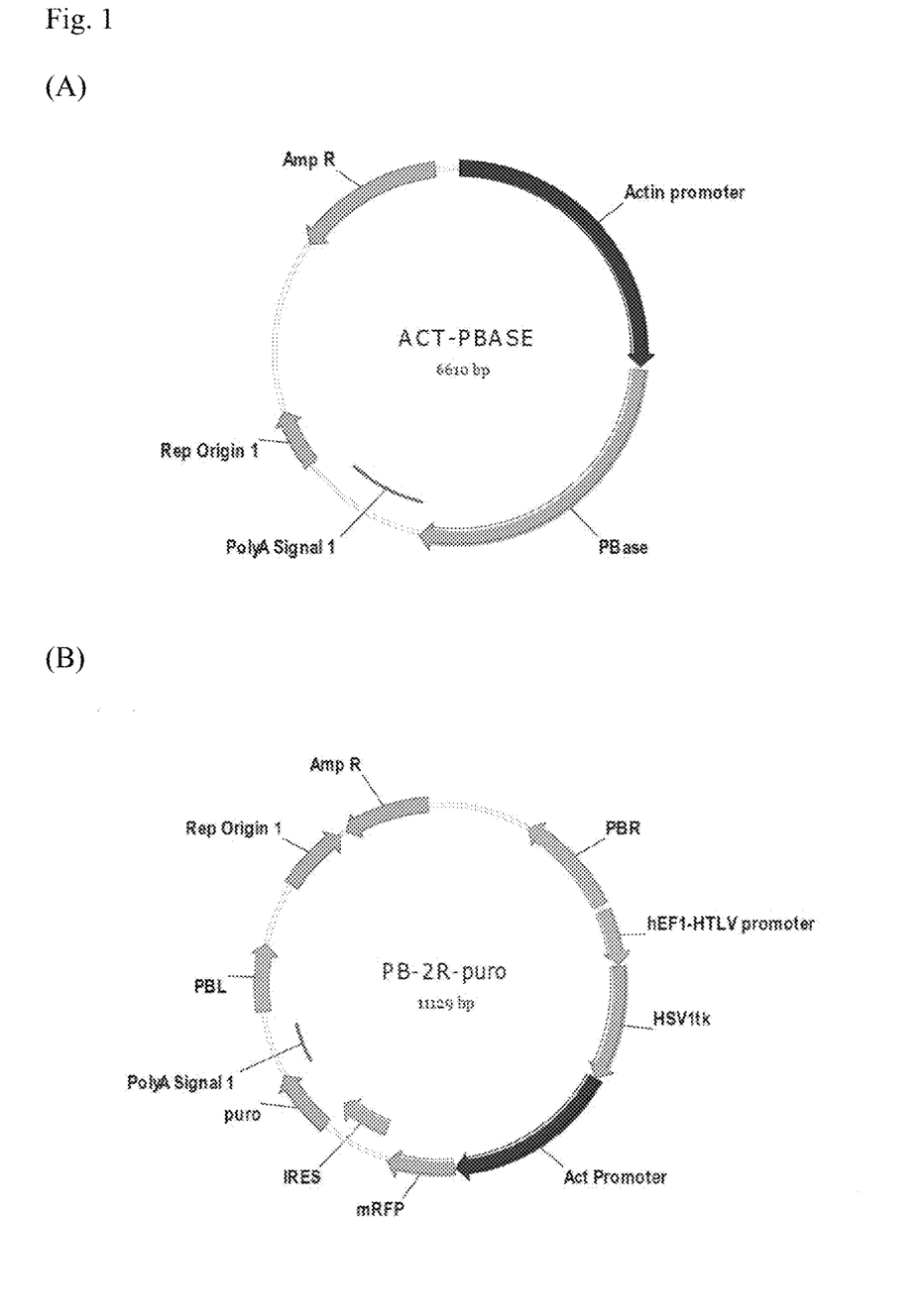
FIG. 1 shows an exemplary piggyBac transposition system for radionuclide-based imaging and optical imaging consists of a helper plasmid Act-PBase (A) and a donor plasmid PB-2R-puro (B).

The PB-tk-mRFP reporter plasmids and Act-PBase helper plasmid were kindly provided by Dr. Congjian Xu (Fudan University, PR China). PB-tk-mRFP was further modified by inserting a puromycin resistance cassette into the BglII and BamHI sites to obtain a new construct named PB-2R-puro. The maps of Act-PBase helper plasmid and PB-2R-puro donor plasmid are showed in FIG. 1(A) and FIG. 1(B), respectively.

4T1 murine breast carcinomas (a kind gift from Dr. Yueh-Hsing Ou at National Yang-Ming University) were cultured in RPMI1640 medium supplemented with 10% (V/V) fetal bovine serum, 100 U/mL of penicillin, and 100 mg/mL streptomycin. The cell lines were maintained at 37° C. in a humidified incubator containing 5% $CO_2$ and were routinely passaged every two days. For co-transfection, donor plasmid PB-2R-puro was mixed with helper plasmid Act-PBase at the optimal ratio and transfected into cells using jetPEI transfection reagent (Polyplus-transfection Inc., New York, N.Y.). Transfected cells were sorted using a BD FACSCalibur system (BD, Franklin Lakes, N.J.) equipped with an air-cooled argon laser excited at 488 nm. The cells were expanded and maintained for further experiments without puromycin selection. For the transposition assay, 4T1 cells were exposed to 8 μg/ml of puromycin for 7 days, and were then fixed using 30% methanol dissolved in 10% acetate (V/V) for 10 min and stained with 1% crystal violet for counting.

Gene transposition mediated by the piggyBac transposon system was validated by genomic PCR and fluorescence in situ hybridization (FISH) analysis targeting the mRFP sequence in the genomes. For genomic PCR, the genomic DNA was extracted using DNAzol® (Invitrogen Inc.). The forward primer and reverse primer for amplifying the mRFP sequence were 5' ccatgggctgggaggcctcc 3' (SEQ ID NO. 1) and 5' ttaaccctagaaagatagtctg 3' (SEQ ID NO. 2), respectively. The PCR product of 0.67 kb was separated on a 1% agarose gel and visualized by ethidium bromide staining. FISH analysis was performed according to previous reports with modification.

Two days after transfection, 0.7-0.9% of mRFP expressing 4T1 cells could be sorted. The expression of reporter genes was sustained in 4T1 cells co-transfected with both plasmids (so called 4T1-PB-2R/PBase cells) for greater than 60 days without puromycin selection, but it was diminished in 4T1 cells transfected with PB-2R-puro only (so called 4T1-PB-2R cells) after 7 days of culture (FIGS. 2(A) and 2(B)).

A transposition assay was also used to confirm the requirement for the Act-PBase helper plasmid in the stabilization of reporter genes in 4T1 cells by puromycin selection. The activity of HSV1-tk expressed in 4T1 cells was determined by a cell uptake assay and MTT (3-[4,5-dimethylthiazol-2-yl]-2, 5diphenylterazoliumbromide) assay. For the cell uptake assay, $1\times10^5$ cells were seeded in 24-well culture plates and cultured overnight. $^3$H-FIAU (1 µCi per well) was then added to each well for 2 hours. The radioactivities in the cells and in the supernatant were determined separately and normalized using a gamma counter (Wallac 1470 Wizard, Perkin Elmer, Waltham, Mass.). For the MTT assay, 800 cells were seeded in 96-well plates and cultured overnight. Different concentrations of GCV (Sigma-Aldrich, Inc. St., Louis, Mo.) were added to the wells and maintained for four days. MTT (1 mg/ml) (Sigma-Aldrich, Inc.) was then added to the cells for four hours, dissolved in dimethyl sulfoxide, and measured at an absorbance of 570 nm on an ELISA plate reader (BIO-TEK instruments, Winooski, Vt.).

Figure 2:
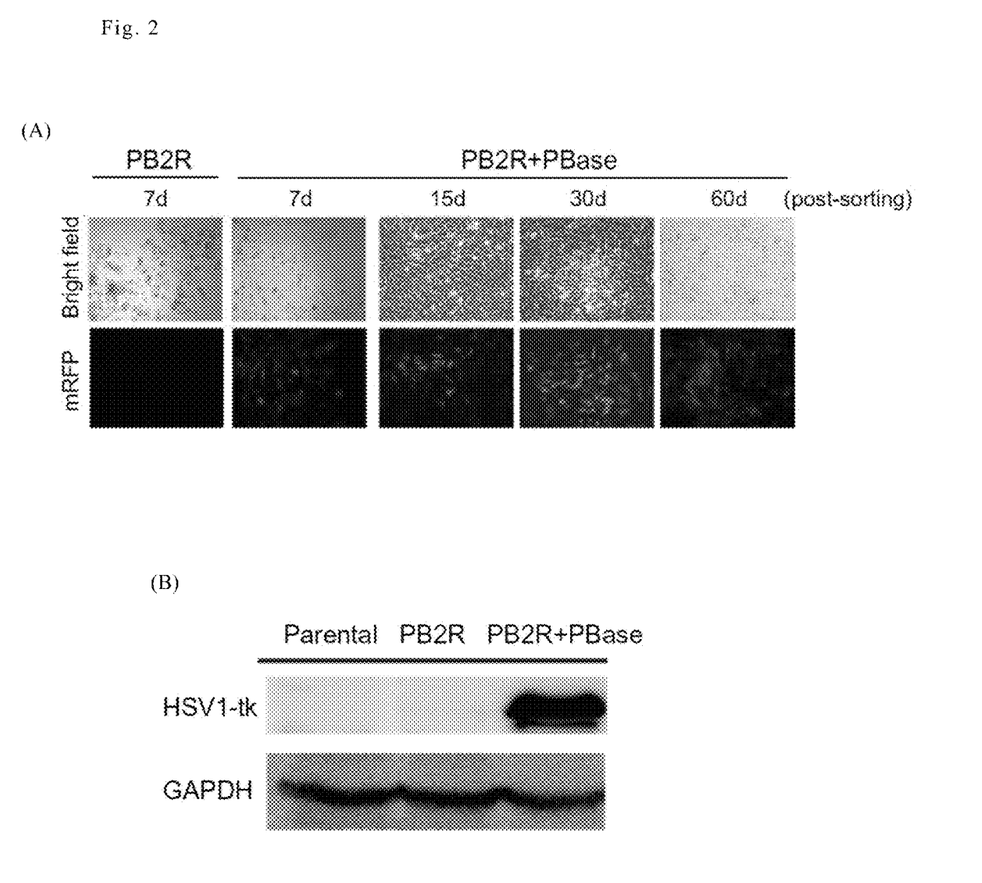
FIG. 2 shows in vitro functional analysis of reporter genes transduced into 4T1 cells using the piggyBac transposon system.

The sustained expression of HSV1-tk in 4T1-PB-2R/PBase cells remained functional as determined by a cell uptake assay using $^3$H-FIAU (FIG. 2(C)). Furthermore, 4T1-PB-2R/PBase cells were sensitive to GCV, which is a prodrug phosphorylated and activated by HSV1-tk to cause cell death (FIG. 2(D)). Additionally, genomic PCR and FISH assays demonstrated that the long-term expression of reporter genes was accompanied by chromosomal integration, as shown by detection of the mRFP DNA fragment in the genomes of 4T1-PB-2R/PBase cells (FIGS. 2(E) and 2(F)). Thus, the 4T1-PB-2R/PBase cancer cells can be used for optical imaging and radionuclide-based imaging in vivo.

Example 2

Monitor and Identify Solid Tumor Remained Cells by PiggyBac Based Multiple Reporter Gene Animal Model Syngeneic Tumor Model Based on the experimental design, different numbers of 4T1 cells and the derived stable cell lines were implanted into 6-week-old female BALB/c mice (National Taiwan University College of Medicine, Taipei, Taiwan) at subcutaneous positions or in the fat pads. The tumor volumes at subcutaneous positions were measured by caliper every 3 days and calculated using the following formula: Volume=Length (mm)×Width$^2$ (mm$^2$)/2. An IVIS50 system (Xenogen Inc. Alamda, Calif.) was used to image the expression of mRFP in the 4T1 tumors. The regions of interest (ROIs) were acquired based on the signals emitted from the tumor positions and semi-quantified as photons/sec. Data quantification was analyzed using the IGOR-PRO Living Imaging Software. The animal use protocols have been reviewed and approved by the institutional animal care and use committee (IACUC) of National Yang-Ming University (approval number: 981225).

Figure 3:
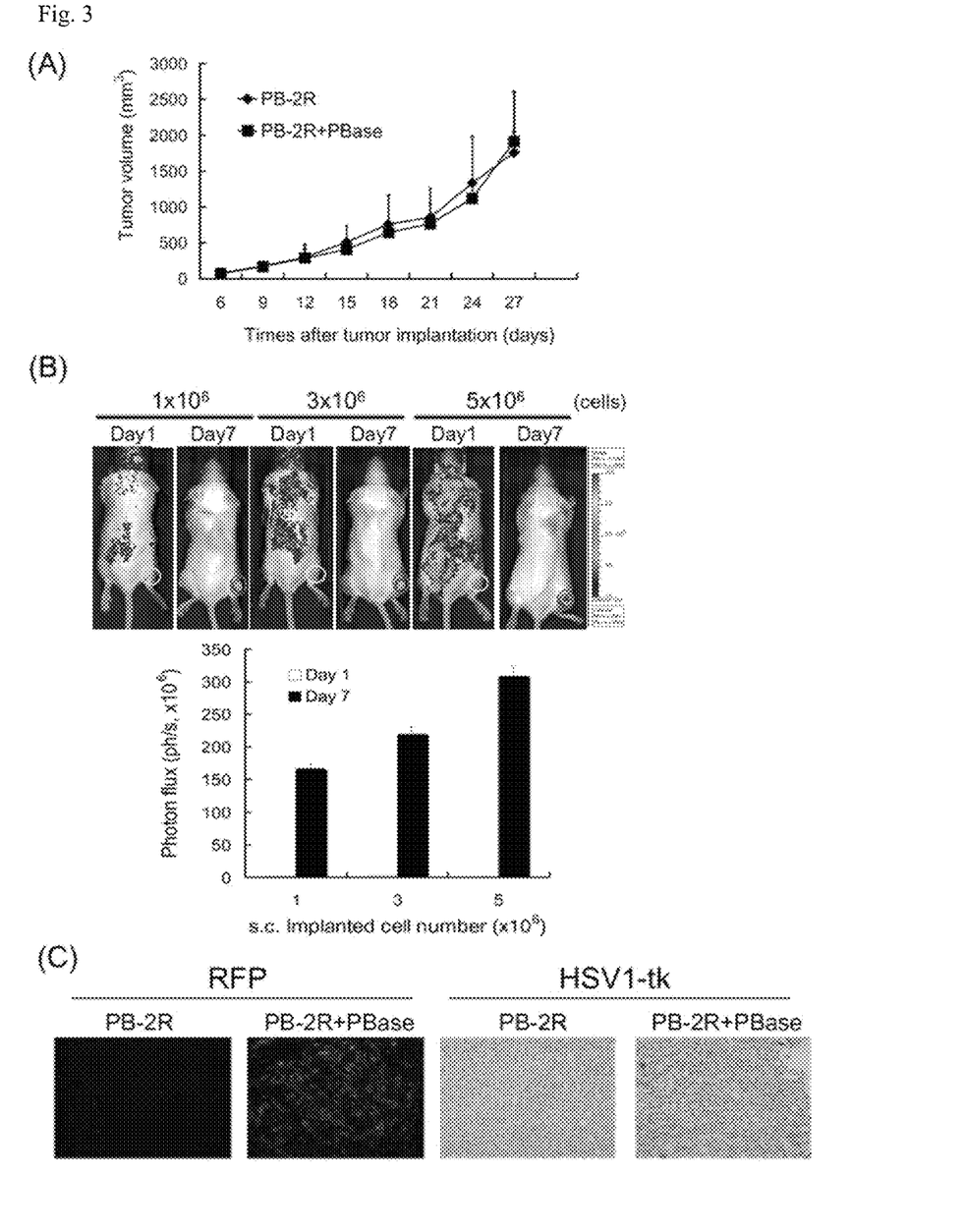
FIG. 3 is a diagram showing the syngeneic tumor model using BALB/c mice.

The growth rates of tumors formed by these two cell types were similar, indicating that genomic integration of reporter genes did not affect cell proliferation (FIG. 3(A)). Although the fluorescent signals were undetectable in animals one day after s.c. injection of both cell types, the signals were detected in 4T1-PB-2R/PBase cells that formed tumors 7 days after implantation but not 4T1-PB-2R cells in a cell number-dependent manner (FIG. 3(B)). These results were further confirmed by histological investigation of mRFP and HSV1-tk expression in the tumors (FIG. 3(C)).

MicroSPECT/CT and MicroPET/CT Imaging

Radionuclide-based tumor imaging acquisition was based on a FLEX Triumph preclinical imaging system (Gamma Medica-Ideas, Inc., Northridge, Calif.) as previously described (Yang FY, et al., 2011, *J Nucl Med.* 52(3):478-484). For microSPECT/CT tumor imaging, mice were given Lugol's solution (potassium iodide tablets) one hour prior to i.v. injection of $^{123}$I-FIAU (16 mCi/kg). Six hours later, the mice were anesthetized using 2% isoflurane mixed with oxygen and scanned by CT using 512 slides for anatomic coregistration. Subsequently, a dynamic SPECT sequence involving 8 frames was conducted. Thirty-two projections (28 seconds) were acquired over 180°, which formed a 60×60 matrix for a total imaging time of 15 minutes per frame. For microPET/CT imaging of 4T1 tumors, mice were injected i.v. with $^{18}$F-FDG (22.7 mCi/kg). CT scanning was performed the same as above and was followed by PET scanning for 45 minutes. The imaging was viewed and reconstructed to obtain a three-dimensional image using free Amide Software (SourceForge, Geeknet Inc., Fairfax, Va.).

Figure 4:
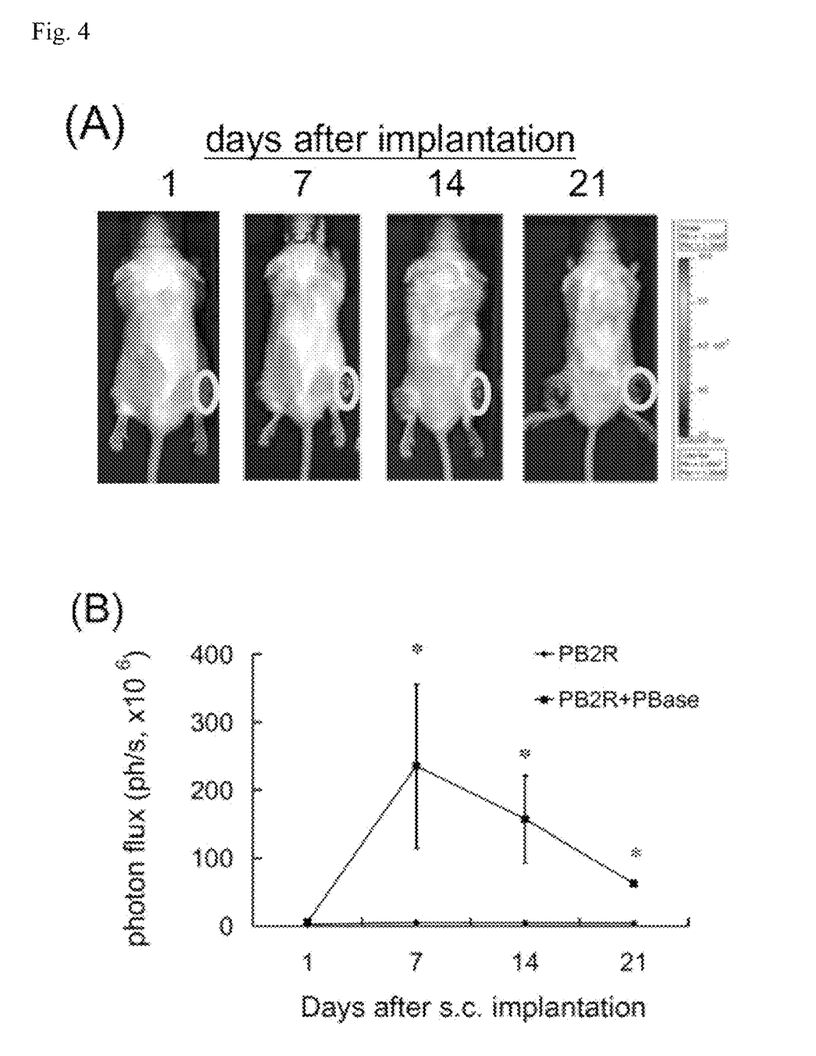
FIG. 4 shows the time-course dependent tracking of live cells in syngeneic tumors by multimodality reporter gene imaging.

Rapid tumor growth is accompanied by an increase in cell loss at the primary site. Reporter gene imaging is ideal for distinguishing the viable cells in vivo because only living cells can transcribe and translate reporter genes. Hence, we tracked the tumor progression in 4T1-PB-2R/PBase cells in a time-dependent manner. One million cells were s.c. implanted in the right thigh of BALB/c mice. Injection of 4T1-PB-2R cells that did not express the reporter genes in the left thigh of the same mouse was used as a control. FIG. 4(A) shows that the maximum mRFP signals were detected at 7 days post-implantation, while the signals gradually decreased until 21 days. The photon emission per second was also semi-quantified at each time point and indicated that the mRFP signals decreased following tumor growth (FIG. 4(B)).

To better understand the positions and characteristics of viable 4T1-PB-2R/PBase cells in implanted tumors, $^{123}$I-FIAU, a radiolabeled nucleotide analogue that emits γ-rays, was i.v. injected to monitor cells expressing HSV1-tk in the tumor mass. The microSPECT/CT imaging showed that the accumulation of $^{123}$I-FIAU in tumors was detected at least one week after implantation, and the ratio of accumulated $^{123}$I-FIAU gradually decreased following tumor growth (FIG. 4(C)).

Reconstruction of 512 imaging slides obtained by microSPECT/CT showed rotatable three-dimensional imaging from week 1 to week 4 after initial implantation (FIG. 4(D)). The 3-D imaging showed that viable cells were not only detected near the side of the body in the implanted tumor, but also spread to different organs following tumor growth. We also exploited $^{18}$F-FDG to confirm the presence of viable cells in the tumor mass using microPET/CT imaging, and the results were consistent with those obtained by SPECT/CT and optical imaging (FIG. 4(E)). The 4-week old tumor was excised and embedded in OCT for frozen sections, and the histopathological staining also showed that the tumor contained viable cells and a necrotic region (FIG. 4(F)). Thus, a combination of dual reporter genes for fluorescent imaging and radionuclide-based imaging can precisely detect live cells for further investigation.

This syngeneic tumor model is ideal for exploring the tumor growth and metastasis in the context of a normal immune system. This model is also especially important for the study of the growth niche for CSCs progression. The 4T1-PB-2R/PBase tumor model contains a HSV1-tk reporter gene that can obtain better spatial resolution for detecting tumor progression using SPECT/CT. Although the optical imaging based on mRFP expression can only detect live cells at surface-deep tumors, mRFP is very important for ex vivo study of these live cells. Examination of mRFP expression using the fluorescent microscope is the most convenient method to confirm that isolated cells originated from the primary tumor ex vivo.

Example 3

The Remnant Live Cells in Solid Tumors Exhibited the Characteristics of Cancer Initiating Cells Cell loss from rapidly growing tumors is caused by intrinsic and extrinsic stresses. However, little is known regarding the properties of the remnant live cells. Because CSCs are resistant to environmental insults, we investigated whether the remnant live cells in solid tumors exhibited the characteristics of CSCs. Based on the results of the multimodality reporter gene imaging described above, ex vivo experiments were performed to isolate the remnant live cells from late-stage tumors formed by 4T1-PB-2R/PBase cells.

To isolate live cells from the tumors, 4-5 week old tumors were removed and rinsed, minced, and then trypsinized to resuspend the cells. After centrifugation, the cell pellets were cultured in RPMI-1640 medium containing 10% FBS and a high concentration of penicillin/streptomycin solution. The isolated cells were validated by visualization of mRFP expression using a fluorescence microscope.

Sphere Formation Assay

Five thousand cells were seeded in a 10-cm non-coated plate. The conditional medium contained serum-free DMEM/F12, 10 ng/ml of epithelial growth factor (EGF), 10 ng/ml of basic fibroblast growth factor (bFGF), 10 ng/ml of insulin and 5 ml of N2 (Gibco Inc. Grand island, N.Y.). Formed spheres were visualized under a bright-field microscope 2 days after the initial seeding.

Figure 5:
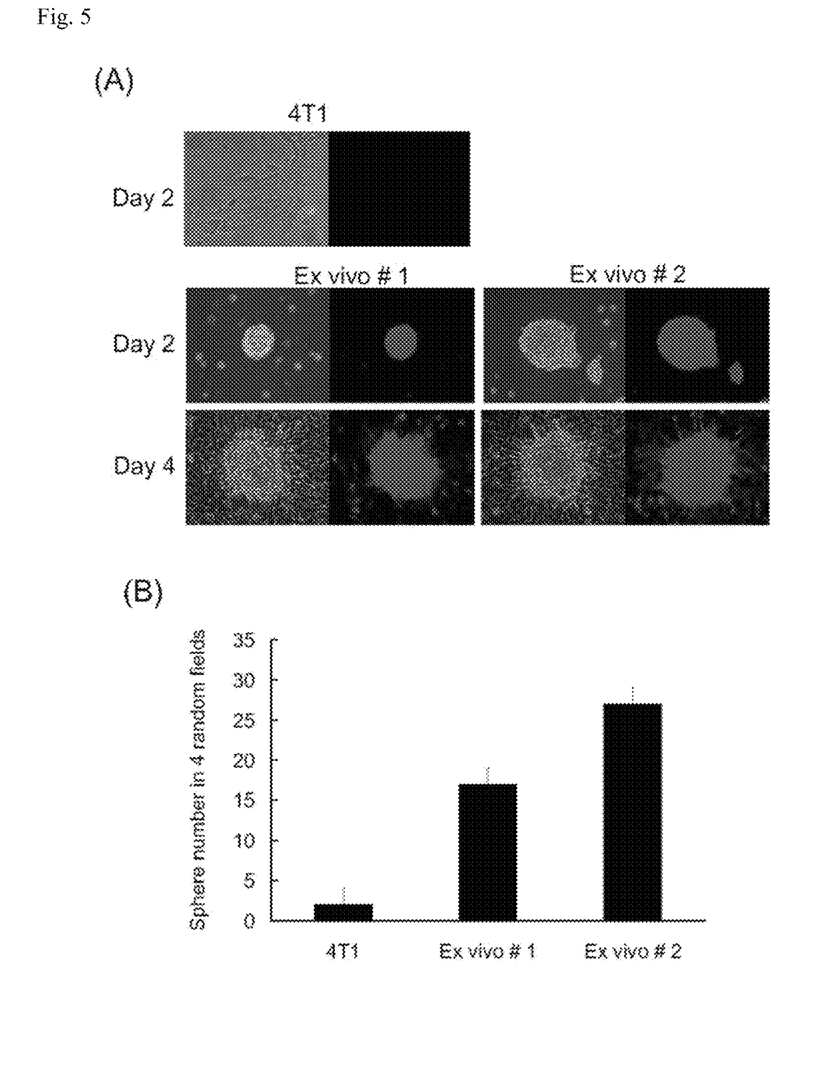
FIG. 5 shows the increase in mammosphere formation by the remnant live cells isolated from late-stage primary tumors.

FIG. 5(A) showed that mRFP-expressing mammospheres were formed in ex vivo 4T1-PB-2R/PBase cells but not in parental 4T1 cells 2 days after seeding. Interestingly, cells started to spread from the mammospheres and form epithelial phenotypes with mRFP after four days. The number of mammospheres from ex vivo 4T1-PB-2R/PBase cells was greater than that of parental 4T1 cells four days after initial seeding (FIG. 5(B)). These observations suggest that remnant live cells in late-stage tumors exhibit CSCs-like characteristics.

Real-Time PCR Aanalysis

Two general CSCs biomarkers, Oct4 and Sox2, were subsequently examined using semi-quantitative real-time PCR (qPCR). Total RNA was extracted using TRIzol® reagent (Invitrogen Inc.). One milligram of total RNA was subjected to cDNA synthesis using SuperScript II reverse transcriptase (Invitrogen Inc.). For real-time qPCR analysis of Oct4 gene expression, the forward primer was 5'-accgagtgagaggcaacc-3' (SEQ ID NO. 3), and the reverse primer was 5'-tgagaaag-gagacccagcag-3' (SEQ ID NO. 4). For the Sox2 gene, the forward primer was 5'-cgagtggaaactttgtcgga-3' (SEQ ID NO. 5), and the reverse primer was 5'-tgtgcagcgtcgcag-3' (SEQ ID NO. 6). The human/mouse beta actin gene was used as an internal control, for which the forward primer was 5'-ggaaatcgtgcgtgacattaag-3' (SEQ ID NO. 7), and the reverse primer was 5'-ggccatctcttgctcgaagt-3' (SEQ ID NO. 8). The experiments were conducted using the Master SYBR Green reagent (Applied Biosystems Inc. Carlsbad, Calif.) mixed with cDNA templates and corresponding primers, and the reactions were performed in a StepOnePlus™ machine (Applied Biosystems Inc.). Compared to parental 4T1 cells, ex vivo 4T1-PB-2R/PBase cells exhibited up-regulation of Oct4 and Sox2 mRNA (FIGS. 6A and 6B).

Oct4 Promoter Assay

The PGL4.2-Oct4 luciferase reporter gene construct containing the human Pou5f (Oct-4) gene promoter was a gift from Dr. Mu-Hwa Yang at National Yang-Ming University. This construct was transfected into cells for 48 hours using jetPEI™ (Polyplus-transfection Inc.) according to the manufacturer's instructions. The transfected cells were lysed with lysis buffer (Promega Inc., Madison, Wis.), and the lysate was subjected to the luciferase assay using 50 mM of D-luciferin. The illuminant intensity was measured using the Wallac Victor 2 Multi-label Counter (Perkin Elmer). Each datum was normalized to the total protein level. From the results shown in FIG. 6C, the transcriptional activity of Oct4 was also increased in ex vivo 4T1-PB-2R/PBase cells (FIG. 6C).

Figure 6:
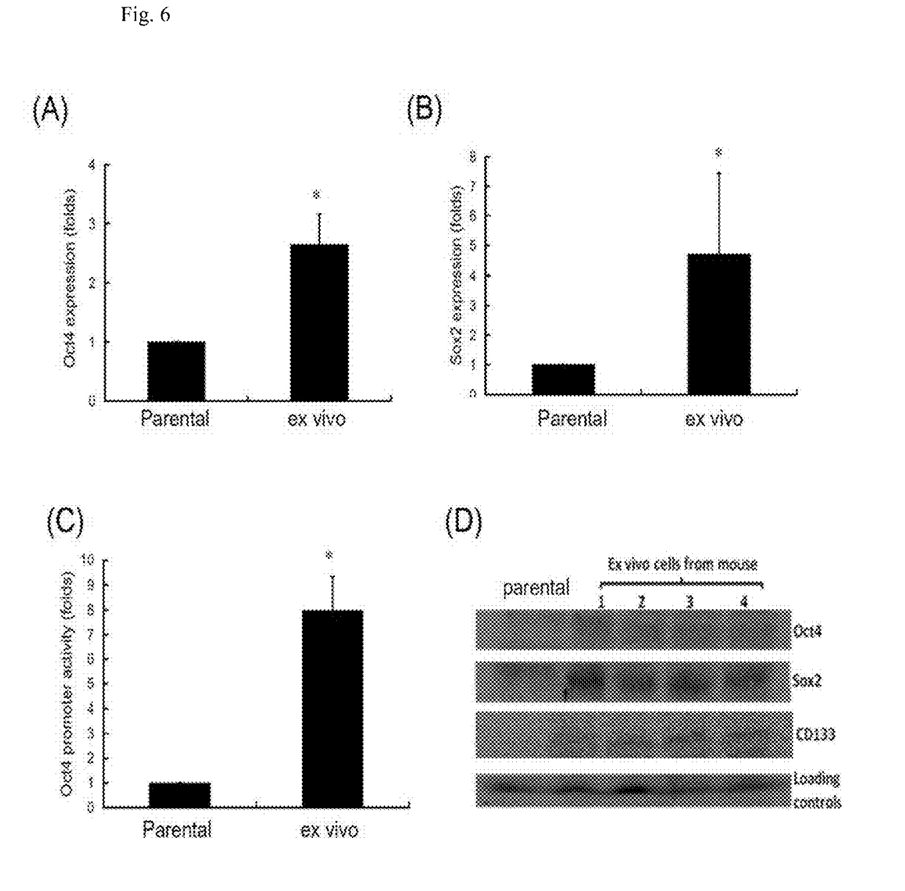
FIG. 6 is the expression of CSC markers in ex vivo isolated remnant live cells from late-stage primary tumors. (A) Oct4 mRNA and (B) Sox2 mRNA expression was compared between parental 4T1 cells and isolated remnant live cells using real-time qPCR.

Furthermore, the protein levels of Oct4, Sox2 and other CSCs-associated biomarkers CD133 were up-regulated in four groups of ex vivo 4T1-PB-2R/PBase cells from different mice (FIG. 6D). Taken together, the cells that escape from cell loss in late-stage tumors display CSCs-like characteristics, at least in part.

In this invention, a proof-of-concept that a similar dual reporter gene imaging approach can be used to track CSCs-like viable cells in a late-stage tumor is provided. In one embodiment as described above, $^{123}$I-FIAU is used as a probe for imaging HSV1-tk expressing cells in a tumor mass using microSPECT/CT, and $^{18}$F-FDG is simultaneously applied to confirm the viability and position of the cells using micro-PET/CT. The use of a conditional-activated gene promoter, such as the Oct4 promoter, to drive mRFP and HSV1-tk reporter genes for molecular imaging may represent a better approach for tracking the CSCs in live cells residing in late-stage tumors. The quantification of optical imaging and radionuclide-based imaging is difficult to combine for better elucidation of the locations of live cells in tumors. A gene encoded near-infrared (NIR) fluorescence protein may be used to substitute for mRFP for this purpose.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for in vivo identification of remnant living cells in late-stage tumors as cancer initiating cells (CICs) in a living rodent animal, comprising steps of:
   (a) providing a multimodality reporter gene imaging system for co-expressing multiple reporter genes, wherein the multimodality reporter gene imaging system is delivered by a piggyBac transposon system comprising a helper plasmid that encodes the piggyBac transposase gene, and a donor plasmid comprising a constitutive gene promoter and two reporter genes for in vivo imaging the transcription and translation activity of genes cloned at the downstream of the constitutive gene promoter and an antibiotic-resistant cassette for transposition assay and stable clone selection;
   (b) co-transfecting the donor plasmid comprising the two reporter genes and the helper plasmid into a cancer cell line;
   (c) implanting the transfected cancer cells into a living rodent animal by subcutaneous (SC) inoculation;
   (d) tracking the tumor progression and location of remnant living cancer cells that escape loss or death in a late-stage tumor bearing in the rodent animal by the multimodality reporter gene imaging;
   (e) isolating the remnant living cells that escape cell loss or death in a late-stage tumor for an assay of sphere formation or cancer initiating cell biomarker genes; and
   (f) identifying the remnant living cells that escape cell loss or death in a late-stage tumor as candidate cancer initiating cells —when the amount of sphere formation and cancer initiating cell biomarker genes increase.

2. The method of claim 1, wherein the antibiotic-resistant cassette comprises at least one anti-neomycine, anti-hygromycine, or anti-puromycine gene.

3. The method of claim 1, wherein the two reporter genes are selected from the group consisted of fluorescence protein gene and extended-spectrum thymidine kinase gene.

4. The method of claim 3, wherein the fluorescence protein gene is monomeric red fluorescence protein (mRFP) gene.

5. The method of claim 3, wherein the extended-spectrum thymidine kinase gene is herpes simplex virus type 1-thymidine kinase (HSV1-tk) gene.

6. The method of claim 1, wherein the constitutive gene encodes a cancer initiating cell biomarker.

7. The method of claim 1, wherein the cancer initiating cell biomarker genes include Oct4, Sox2, and CD133 genes.

8. The method of claim 1, wherein the location of cancer initiating cells is elucidated by the combination of optical imaging and radionuclide-based imaging.

9. The method of claim 1, which further comprises the assessment of mammosphere formation ability of the remnant living cells in late-stage tumor mass.

* * * * *